United States Patent
Crosbie

(10) Patent No.: US 11,222,036 B1
(45) Date of Patent: Jan. 11, 2022

(54) DATA WAREHOUSE ACCESS REPORTING

(71) Applicant: Amazon Technologies, Inc., Seattle, WA (US)

(72) Inventor: Christopher Patrick Crosbie, Seattle, WA (US)

(73) Assignee: Amazon Technologies, Inc., Seattle, WA (US)

(*) Notice: Subject to any disclaimer, the term of this patent is extended or adjusted under 35 U.S.C. 154(b) by 208 days.

(21) Appl. No.: 14/970,377

(22) Filed: Dec. 15, 2015

(51) Int. Cl.
  *G06F 16/25* (2019.01)
  *G16H 10/60* (2018.01)
  *G06F 16/9535* (2019.01)
  *G06F 16/2453* (2019.01)

(52) U.S. Cl.
  CPC ...... *G06F 16/254* (2019.01); *G06F 16/24542* (2019.01); *G06F 16/9535* (2019.01); *G16H 10/60* (2018.01)

(58) Field of Classification Search
  CPC ......... G06F 17/30563; G06F 17/30463; G06F 17/30867; G06F 16/254; G06F 16/24542; G06F 16/9535; G16H 10/60
  USPC ........................................ 707/602
  See application file for complete search history.

(56) References Cited

U.S. PATENT DOCUMENTS

| | | | |
|---|---|---|---|
| 7,720,804 B2 * | 5/2010 | Fazal | G06F 16/248 707/601 |
| 9,836,507 B2 * | 12/2017 | Hu | G06F 16/24544 |
| 2003/0055813 A1 * | 3/2003 | Chaudhuri | G06F 16/24545 |
| 2004/0133568 A1 * | 7/2004 | Witkowski | G06F 40/18 |
| 2008/0071748 A1 * | 3/2008 | Wroblewski | H03M 7/30 |
| 2008/0133458 A1 * | 6/2008 | Zabback | G06F 16/24545 |
| 2009/0144337 A1 * | 6/2009 | Barsness | G06F 17/30377 |
| 2011/0276674 A1 * | 11/2011 | Jensen-Horne | G06F 9/5061 709/223 |
| 2013/0238596 A1 * | 9/2013 | Mandelstein | G06F 17/30563 707/714 |
| 2013/0275365 A1 * | 10/2013 | Wang | G06F 16/283 707/602 |
| 2014/0258266 A1 * | 9/2014 | Cruanes | G06F 16/24542 707/718 |
| 2016/0034530 A1 * | 2/2016 | Nguyen | G06F 16/2471 707/719 |

* cited by examiner

*Primary Examiner* — Hosain T Alam
*Assistant Examiner* — Saba Ahmed
(74) *Attorney, Agent, or Firm* — Davis Wright Tremaine LLP

(57) ABSTRACT

A database table may include a column associated with metadata indicative of a requirement to audit access to rows of the table. When a database receives a query, a query optimizer may determine that rows of the table will be accessed when the query is processed. The query optimizer may form a query plan that includes instructions for retrieving data for the column that is needed for generating an audit record for each row accessed. The column associated with the metadata may be included in the record.

20 Claims, 10 Drawing Sheets

DATA WAREHOUSE ACCESS REPORTING

BACKGROUND

Security and privacy concerns may sometimes be addressed by auditing access to sensitive data. In some instances, moreover, auditing access to sensitive data is a requirement under certain laws or regulations. The Health Insurance Portability and Accountability Act ("HIPAA"), for example, may require auditing access to a patient's records. The auditing may, for example, include forming an audit log entry that has information identifying the record that was accessed.

Compliance with a reporting requirement may be more challenging in data warehouse systems than in transactional databases. One reason for this is that, in a transactional system, the data that is subject to a reporting requirement may be stored in a base table that is generally known to be subject to the reporting requirement. Typical database or application logging mechanisms may, in such cases, be sufficient to comply with the reporting requirement. However, in a data warehouse data from various base tables may be combined, aggregated, or otherwise processed to form new tables that nevertheless contain or reflect data that is subject to the reporting requirement.

BRIEF DESCRIPTION OF DRAWINGS

The following detailed description may be better understood when read in conjunction with the appended drawings. For the purposes of illustration, various examples of aspects of the disclosure are shown in the drawings; however, the invention is not limited to the specific methods and instrumentalities disclosed.

DETAILED DESCRIPTION

Described herein are systems, methods, and computer program products for auditing access to data maintained in a database. In an example, data maintained in a database component of a data warehouse is subject to a reporting requirement, such as one that might be imposed by HIPAA. Of the tables maintained in the database, only a subset may be subject to the reporting requirement. Of those tables, a subset of columns may be stored in auditing records produced for compliance with the reporting requirement. Those columns may be marked, in column metadata, with a flag indicating that the column is "traceable." By way of association with columns so marked, it may be inferred that the table containing those columns is subject to a reporting requirement.

The reporting requirement may involve reporting on different levels of access. For example, in some cases, a reporting requirement may indicate that access to data is to be audited whenever that data is explicitly included in a generated report or other result set. In other cases, however, the reporting requirement might indicate that access to the data should be audited even when the data is not included in a report. For example, data subject to a reporting requirement may be excluded from any of the projections specified by the query, but nevertheless accessed in some other way when the query is processed. The reporting requirement might, in some cases, indicate that access should be audited when a record is used to produce aggregate data. For example, a reporting requirement might specify that a patient be notified whenever his data is used, even if that data is anonymized. An audit record might be generated, in that case, when the patient's record is accessed during the anonymizing process.

In an example embodiment, a query optimizer forms a query plan in a manner that is cognizant of potential auditing requirements. A query plan may comprise instructions for performing various operations needed to process the query and obtain a result set. The query optimizer may examine column metadata to identify columns that have been marked as traceable. Based on identifying these columns, the query optimizer may infer that a table or view associated with the columns so marked is subject to a reporting requirement. The query optimizer may add or modify instructions in the query plan so that the query plan, when executed, retrieves data needed for auditing and stores the information needed for the audit. For example, a scan operation specified by instructions in the query plan might be expanded to include additional columns needed for auditing. The query optimizer might also add operations for performing the auditing itself. For example, the query optimizer might add operations to the plan that cause audit records to be generated and stored in an audit log.

Figure 1:
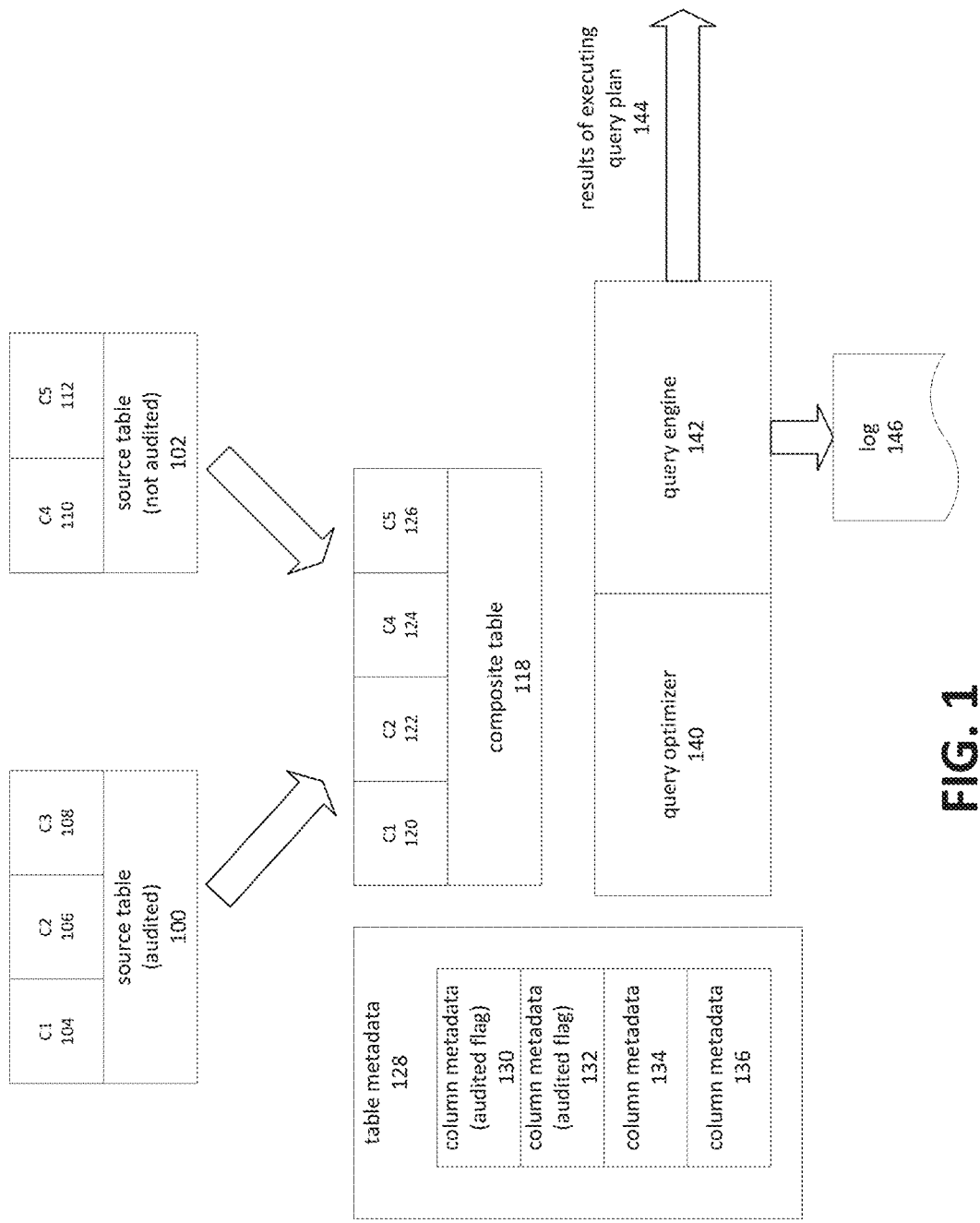
FIG. 1 is a block diagram depicting a data warehouse maintaining data subject to a reporting requirement.

FIG. 1 is a block diagram depicting a data warehouse maintaining data subject to a reporting requirement. In a data warehouse, various source tables 100, 102 may be combined to form a composite table 118. The composite table 118 might include columns C1, C2, and C3 104, 106,108 from source table 100 and columns C4 and C5 110, 112 from source table 102. It may further be the case that data in source table 100 is subject to a reporting requirement. For example, there may be a legal, regulatory, or other requirement for collecting and reporting on access to the data stored in the source table 100. Other tables, such as the source table 102, may not be subject to a reporting requirement.

When data is combined into composite table 118, the data subject to a reporting requirement may remain subject to the reporting requirement. For example, if columns C1 and C2 104, 106 in source table 100 are subject to a reporting requirement, columns C1 and C2 120, 122 in composite table 118 may also be subject to the reporting requirement. In some cases, the reporting requirement may extend to all columns C1, C2, C4, and C5 120-126 in the composite table 118.

The data warehouse may maintain table metadata 128 corresponding to the composite table 118. The table metadata 128 may include information indicating that data in the composite table 118 is subject to the reporting requirement. For example, column metadata 130 corresponding to column C1 120 may indicate that column C1 120 is subject to a reporting requirement, and column metadata 132 may indicate that column C2 122 is subject to the reporting requirement. Columns C4 and C5 124, 126 may have corresponding column metadata 134, 136 that does not indicate that the data in columns C4 and C5 124, 126 is subject to the reporting requirement. However, columns C4 and C5 124, 126 may be treated as subject to the reporting requirement based on their association with columns C1 and C2 120, 122.

A query optimizer 140 may form query plans that define instructions for operations to be performed to execute a query. The query plan may be formed, for example, by parsing a textual representation of a query and determining, based on the parsed query, a sequence of operations could be performed to obtain results for the query. The operations may be expressed as a program, graph, network, or some other form that allows for the sequence of operations to be expressed, potentially included conditional operations, branching, and so forth. The aforementioned structure thus describes a set of instructions for processing the query.

The query optimizer 140 may adapt its operation based on detecting the presence of a flag that is indicative of the reporting requirement. For example, the column metadata 130, 132 for columns C1 and C2 120, 122 may include a "traceable" flag that can indicate that data in the composite table 118 are subject to a reporting requirement. The query optimizer 140 may identify the presence of the column metadata 130, 132 and determine, based on that presence, that access to any of the columns 120-126 of composite table 118 should be reported. In some cases, access may be reported even when no projection specified by the query includes any of the columns 120-126 in the composite table 118. The query optimizer 140 may also determine, based on the column metadata 130, 132, that a report of the access should comprise the columns 120, 122 that correspond to the column metadata 130, 132 that have the "traceable" flag.

The query optimizer 140 may form or modify a query plan based on the presence of the flag. For example, the query optimizer may cause the query plan to include an operation that retrieves data for columns C1 and C2 120, 122. When the query plan is then executed, data required for reporting may then be available. The query optimizer 140 may also incorporate cognizance of the retrieval of data for columns C1 and C2 120, 122 into formation of the query plan, so that overall performance of the query plan is maximal, given the data that must be retrieved and processed for reporting purposes.

A query engine 142 may process the query plan generated by the query optimizer 140. The query plan processed by the query engine 142 may include operations for obtaining the results of executing the query 144, obtaining data necessary for compliance with the reporting requirement, and writing the reporting data to log 146.

Figure 2:
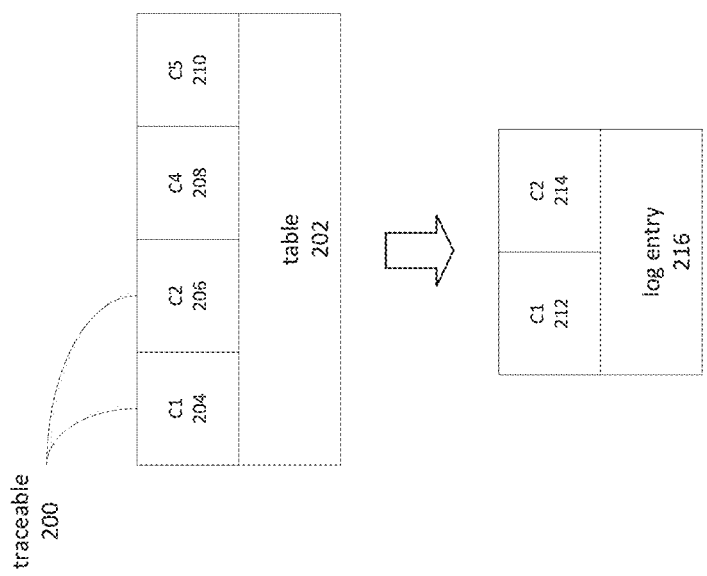
FIG. 2 is a block diagram depicting an example of forming a log entry based on a column metadata flag.

FIG. 2 is a block diagram depicting an example of forming a log entry based on a column metadata flag. In the example of FIG. 2, a table 202 may include four columns C1, C2, C4, and C5 204-210. Of these columns 204-210, columns C1 and C2 204, 206 are associated with a "traceable" flag 200 stored in column metadata. In various instances, access to any one of rows C1-C4 204-210 may cause a query engine to form a log entry 216 to report access to a row of the table 202. In other words, association of table 202 with column metadata may cause the query engine to store the log entry 216.

The log entry 216 may comprise values for columns C1 and C2 212, 214. The log entry 216 may, for example, be formed by a query engine during execution of the query plan. The log entry 216 may be formed as information appended to a log file, a row inserted into a database table, a record kept in memory, a record transmitted to a queue, and so forth.

Figure 3:
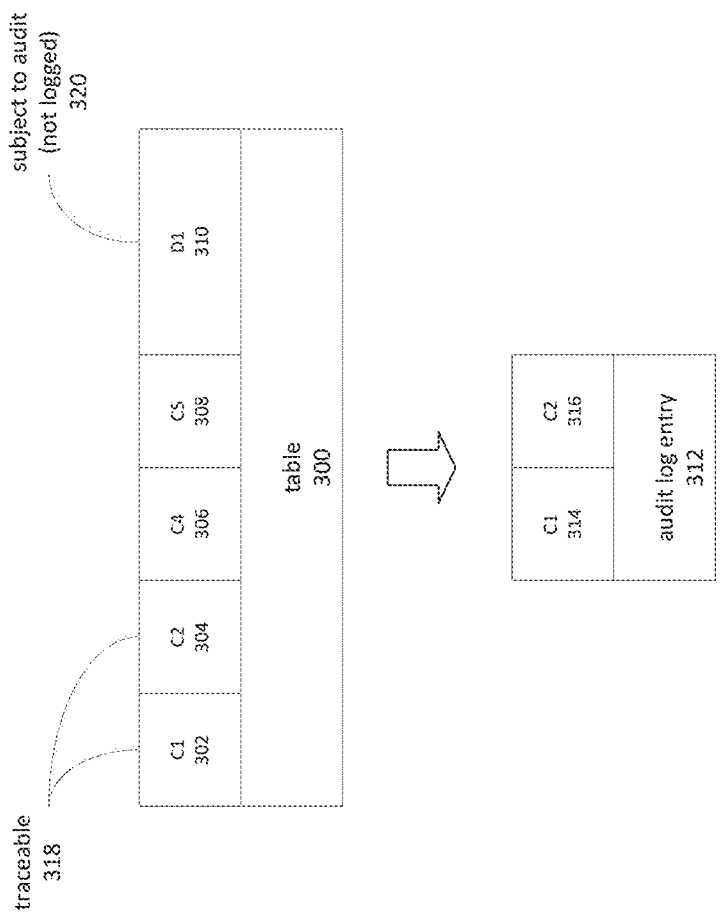
FIG. 3 is a block diagram depicting an example forming a log entry consisting of a subset of data that is subject to a reporting requirement.

FIG. 3 is a block diagram depicting an example forming a log entry consisting of a subset of data that is subject to a reporting requirement. In the example of FIG. 3, columns C1 and C2 302, 304 may be columns obtained from another table whose data is subject to a reporting requirement. The same may be true of column D1 310. However, although column D1 310 may trigger a reporting event when it is accessed, column D1 310 may not be included in the audit log entry 312. This might be the case when only columns C1 and C2 302 and 304 are used to identify the entity affected by the event. For example, HIPAA compliance might involve recording an identifier of a patient whose record was accessed, and an identifier of the record that was accessed. In some instances, additional information such as the date and time of the access might also be included in the audit log entry 312. However, some columns, such as column D1 310, may not be preserved in the audit log entry 312. These may not be preserved because they may be obtained later using other information (e.g. the primary key of the corresponding row), or because recording the information is not required under the reporting requirement. Accordingly, in the example of FIG. 3 the audit log entry 312 may comprise column Cl 314 corresponding to column Cl 302 and column C2 316 corresponding to column C2 304. Column D1 310, on the other hand, might trigger generation of the audit log entry 312 but not be included in the audit log entry 312. The audit log entry 312 may also contain additional metadata, such as the time of an access, a reason for the access, and so forth. In some cases, the query optimizer and/or query engine might ensure that certain data has been collected before permitting access to a row. For example, the query optimizer and/or query engine might check to see that a reason for the access has been provided, and to deny access to the row if a reason for the access has not been provided. The reason for the access may, in some instances, be provided in the query in which the access is requested.

Figure 4:
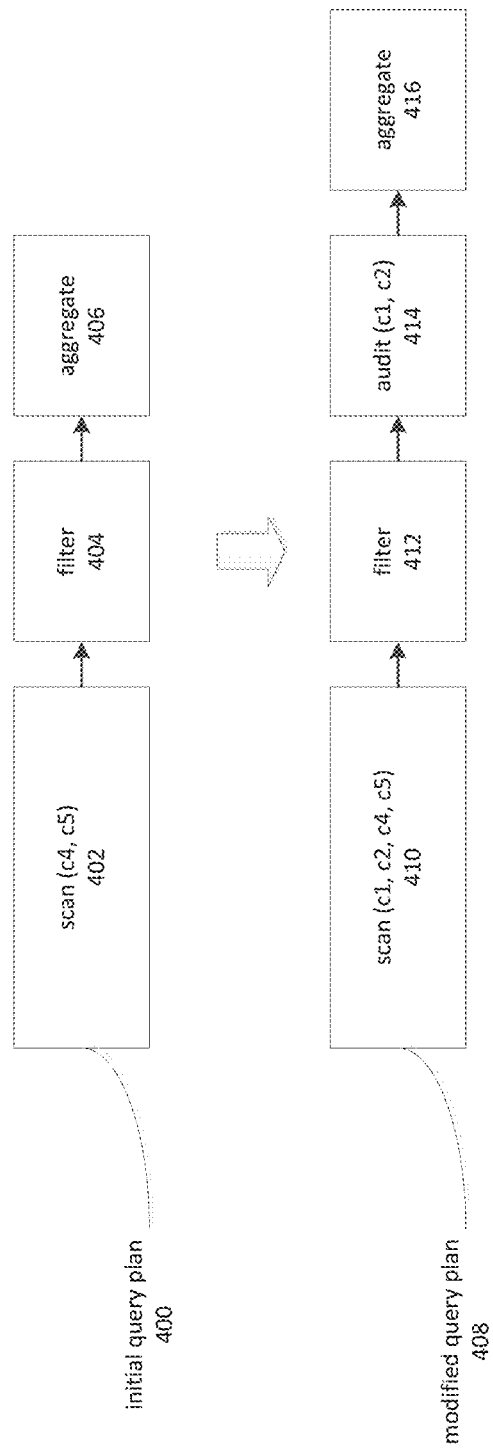
FIG. 4 is a block diagram depicting an example of a query plan that includes auditing-related operations.

A query optimizer may form a query plan based on an input query and modify the plan to retrieve records that are needed for the audit log entry. FIG. 4 is a block diagram depicting an example of forming a query plan that includes auditing-related operations.

An initial query plan 400 may comprise operations for forming a set of results that correspond to a query supplied to the query optimizer. For exemplary purposes, the query may be presumed to relate to selecting data from a table, filtering the selected data, and aggregating the results. This example is intended only to be illustrative and should not be viewed as limiting the scope of the present disclosure. The query optimizer may form a query plan based on the query. The initial query plan 400 may, for example, be formed from the query. The initial query plan 400 might comprise a scan operation 402 pertaining to columns C4 and C5, where columns C4 and C5 are columns of a table that are subject to a reporting requirement. The initial query plan might also specify a filter operation 404 in which rows returned from the scan are filtered based on some criteria, such as a criteria that might be specified in a SQL "WHERE" clause. The initial query plan 400 might also include an aggregate 406 operation, in which summation, averaging, or other aggregating operations are performed on the filtered results.

The query optimizer might alter or modify the initial query plan 400 to change existing operations and add additional operations pertaining to fulfilling the reporting requirement. For example, the query optimizer might form a modified query plan 408 based on the initial query plan 400. Note, however, that the description of an initial query plan 400 and a modified query plan 408 is intended to be illustrative of changes to query plan generation associated with the present disclosure. As such, the depiction should not be viewed as requiring that formation of the initial query plan 400 and the modified query plan 408 be performed in discrete stages. The final modified query plan 408 may, for example, be formed without first forming a query plan that does not include auditing-related operations.

The modified query plan 408 may also contain a scan operation 410 corresponding to the scan operation in the initial query plan 400. The scan operation may comprise traversing a storage device or memory to examine the rows of a table, or of an index over a table. To support the auditing operation, the scan operation 410 may specify a scan of a structure that includes not only C4 and C5 (as was the case with scan operation 402 in the initial query plan 400), but also C1 and C2. In some cases, the query optimizer might add additional columns to the data to be retrieved during the scan. In other cases, the target of the scan operation may change. For example, while an index scan may have been sufficient to retrieve columns C4 and C5, a full table scan might be required to retrieve columns C1 and C2 in addition to C4 and C5.

The filter operation 412 may, in some cases, be similar to the filter operation 404 in the initial query plan 400. However, in other cases the filter operation might be modified so that an appropriate subset of columns C1 and C2 is retained for use in an auditing operation. Although not shown in FIG. 4, in some cases additional filtering operations, or other operation types, might be added to ensure that the appropriate data is available for use with reporting while still limiting the result set to the requested data.

The query optimizer might also insert an audit operation 414 into the query plan. The auditing operation 414 might write data for the appropriate columns into a structure that is suitable for auditing, such as a file, database table, or queue. As depicted by FIG. 4, auditing operation 414 involves columns C1 and C2. The auditing operation 414 is depicted as occurring prior to the aggregate operation 416. The query optimizer may locate the auditing operation 414 prior to the aggregation operation 416 in order based on a requirement to report access to a record even if the record is ultimately not directly included in a result set. For example, a query that calculates average per-patient cost of care might access a particular patient's medical records, even if the data is subsequently depersonalized or converted into non-personally identifiable information.

Figure 5:
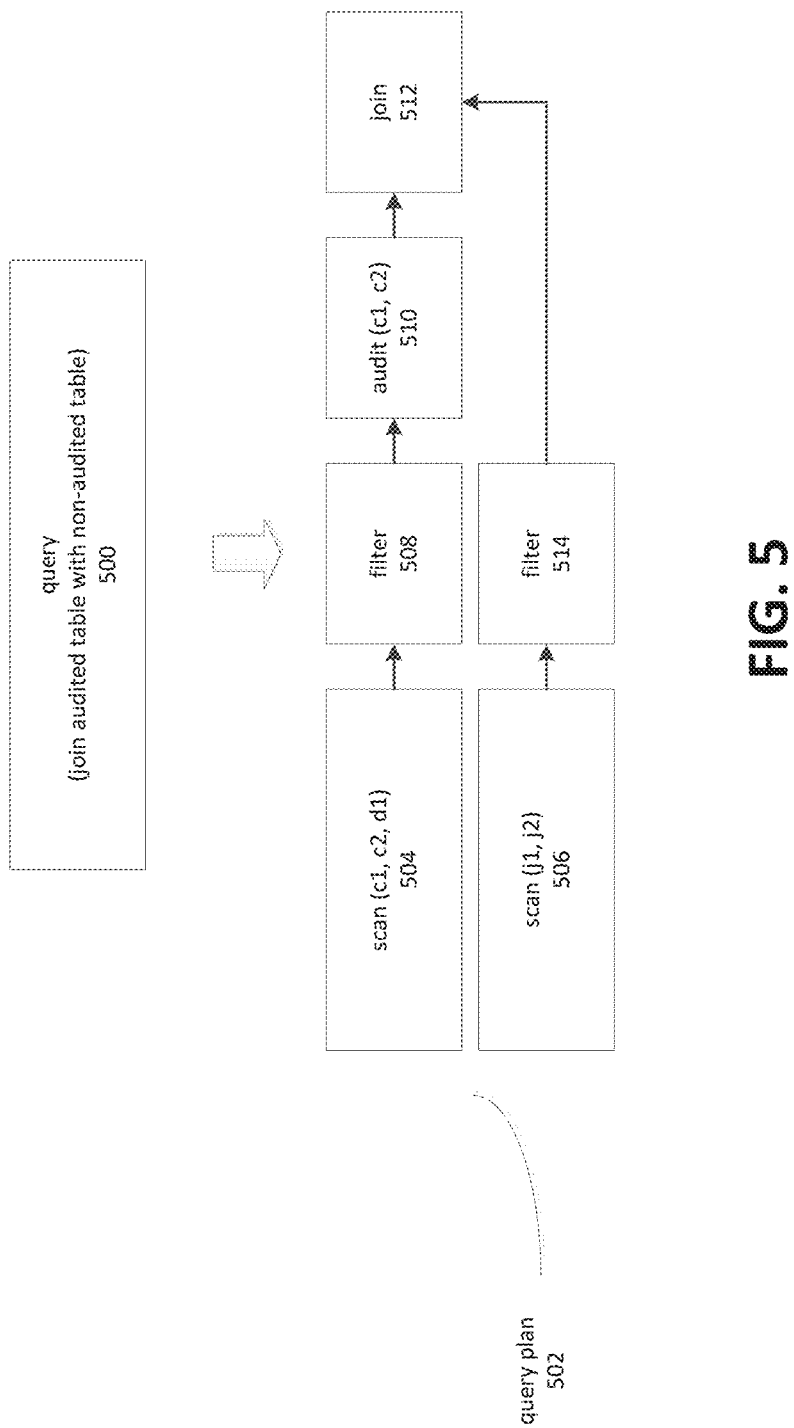
FIG. 5 is a block diagram depicting an additional example of forming of a query plan comprising auditing operations.

FIG. 5 is a block diagram depicting an additional example of forming of a query plan comprising auditing operations. A query 500 may, as depicted in the example of FIG. 5, specify a join operation between a table that is subject to a reporting requirement and another table not subject to the reporting requirement. In other words, the join may be between an audited table and another table that is not audited.

A query plan 502 generated by the query optimizer, based on the query 500, might then contain two scan operations 504, 506 and two filter operations 508, 514. An audit operation 510 might be inserted for auditing columns c1 and c2 of the audited table, prior to the join operation 512. The query optimizer may place the audit operation 510 into this position of the query plan based on the availability of the data needed for auditing in the pipeline of data generated and operated on during execution of the query plan 502.

Figure 6:
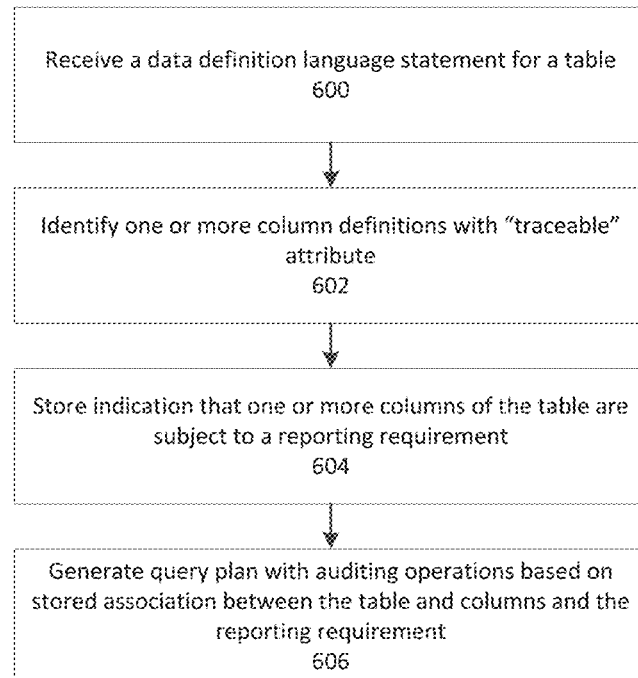
FIG. 6 is a flow diagram depicting an example of associating a table with metadata corresponding to a reporting requirement.

The query optimizer may access table and column metadata to determine whether a table or column is subject to a reporting requirement, and to modify or otherwise form the query plan with operations for complying with the reporting requirement. FIG. 6 is a flow diagram depicting an example of associating a table with metadata corresponding to a reporting requirement. Although depicted as a sequence of blocks, those of ordinary skill in the art will appreciate that the depicted order should not be construed as limiting the scope of the present disclosure and that at least some of the operations referred to in the depicted blocks may be altered, omitted, reordered, supplemented with additional operations, or performed in parallel. Embodiments of the depicted process may be implemented using various combinations of computer-executable instructions executed by a computing system, such as the computing systems described herein.

Block 600 depicts a data warehouse system receiving a data definition language statement. The data definition language statement may specify the structure and other attributes of a table. This may include column definition data, such as the name of a column, the column's data type, and so on. Note that although block 600 depicts receiving a data definition language statement for a table, in other cases data definition language statements may pertain to columns, indexes, views, and so on.

As depicted by block 602, the data warehouse system may identify columns defined as "traceable" by the data definition language statement. In some instances, a column definition may include a "traceable" flag. The traceable flag may, in some instances, indicate that the table as a whole is subject to a reporting requirement—that is, that access to any column of a row should be audited. The traceable flag may further indicate that the particular column marked as traceable should be included in an audit record. For example, the primary key of a table might be marked as traceable. If any column of a row of the table is accessed, the corresponding primary key value may be stored in an audit log.

Block 604 depicts that the data warehouse may store an association between the columns of the table, and/or the table itself, and the reporting requirement. In some cases, the data warehouse may store a record indicating that the table is subject to a reporting requirement and that column X, Y, and Z (for example) are, as indicated by being marked with the traceable flag, to be stored in an audit record once for every time a row of the table is accessed.

Block 606 depicts that the data warehouse, typically by a query optimizer, may generate a query plan comprising auditing operations based on the stored association between the table and columns and the reporting requirement. For example, the query optimizer might initiate generation of a query plan for a query of table T. If the columns A, B, X, Y, and Z are to be accessed, and if columns X, Y, and Z are associated with the "traceable" flag, then access to a row of table T might be audited. Based on the association between columns X, Y, and Z and the traceable flag, the query optimizer might construct a query plan that ensures that values for columns X, Y, and Z are generated for each row of table T that is accessed.

Figure 7:
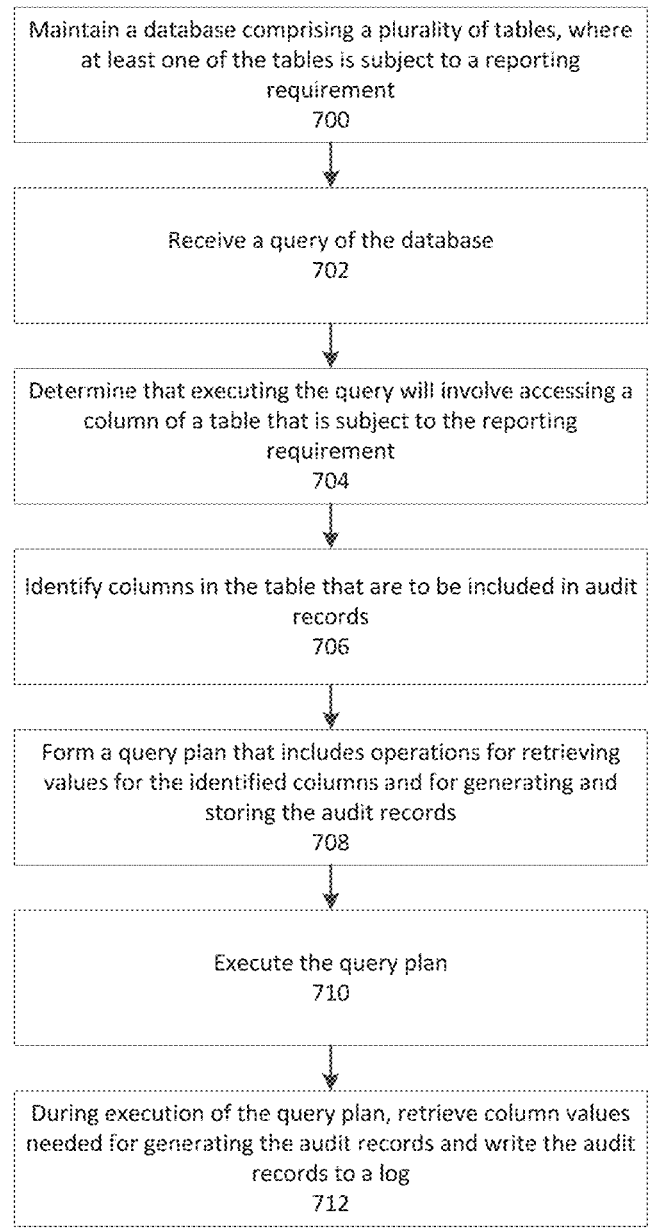
FIG. 7 is a flow diagram depicting an example of compliance with a reporting requirement during execution of a query.

FIG. 7 is a flow diagram depicting an example of compliance with a reporting requirement during execution of a query. Although depicted as a sequence of blocks, those of ordinary skill in the art will appreciate that the depicted order should not be construed as limiting the scope of the present disclosure and that at least some of the operations referred to in the depicted blocks may be altered, omitted, reordered, supplemented with additional operations, or performed in parallel. Embodiments of the depicted process may be implemented using various combinations of computer-executable instructions executed by a computing system, such as the computing systems described herein.

A data warehouse may comprise a database that includes a plurality of tables. As depicted by block 700, a database may comprise a plurality of tables, one or more of which may be subject to a reporting requirement. The reporting requirement may, for example, involve generating an audit log entry once each time a row of a table is accessed. Compliance with the reporting requirement may, in some cases, be made by forming the audit log entry so that it comprises a subset of the table's columns. The subset may, for example, be identified by a "traceable" flag set in the corresponding columns' metadata. The table being subject to the reporting requirement may, in some cases, be inferred based on an association between the table and the columns of the table that are marked with the "traceable" flag.

As depicted by block 702, the data warehouse may receive a query of the database. The query may refer to a table that is subject to the reporting requirement. One example of a query that refers to the table is "select * from T1," where T1 is the table that is subject to the reporting requirement. Note that in this query, the results directly include the contents of the table T1. As such, each row in the result set may correspond to an audit log entry. Another example is "select * from T2 where T2.col1 IN (select T1.col1 from T1). Here, the result set only includes values from the table T2, but T1 was accessed in order to generate those results. In some instances, the access to T1 may be audited.

Block 704 depicts that the data warehouse may determine that processing the received query will involve access to the table that is subject to the reporting requirement. This operation may, in some cases, be performed by a query optimizer component or an algebrizer. This operation may be performed in conjunction with the operation depicted by block 706. As depicted by block 706, the data warehouse may identify columns of the table that are to be included in audit log records. This operation may, for example, be performed by a query optimizer. The query optimizer may examine table and column metadata to determine if the table is subject to a reporting requirement and to identify columns that should be included in audit log entries. For example, the query optimizer may examine column metadata to identify the presence of a "traceable" flag.

As depicted by block 708, the data warehouse may form a query plan so that the query plan includes operations for retrieving data needed for auditing and includes operations for performing the auditing itself. These steps may be performed, for example, by a query optimizer. The data needed for auditing may be included and considered in the various phases of optimization, such as algebrization, cost minimization, and so on.

The data warehouse may then execute the query plan, as depicted by block 710. For example, a query engine may receive the query plan and execute the operations it describes. The data warehouse may, in some cases, include distributed databases. If so, it may be the case that the query plan is distributed to multiple database nodes and executed, in whole or in part, on the database nodes. The query plan sent to each node may or may not contain operations pertaining to auditing, depending upon a variety of factors such as whether or not the particular database node maintains data that is subject to the reporting requirement.

During execution of the query plan, data needed for auditing may be retrieved. Block 712 depicts this. The data retrieval may typically be integrated with retrieval of other data needed for processing a query. For example, if the results of a query are to include columns X and Y, but Z is also needed for auditing, then an index scan included in a query plan may include not only X and Y, but also Z. Note that in some cases, the addition of Z might cause the index scan to be "promoted" to a more costly full table scan. However, the full table scan may be more efficient, in some cases, than retrieving data for column Z separately from X and Y.

Block 712 also depicts that the auditing operations may be performed while the query is being executed. Auditing operations may, for example, be included as steps in the query plan. The steps may then be performed while the query plan is being executed.

Figure 8:
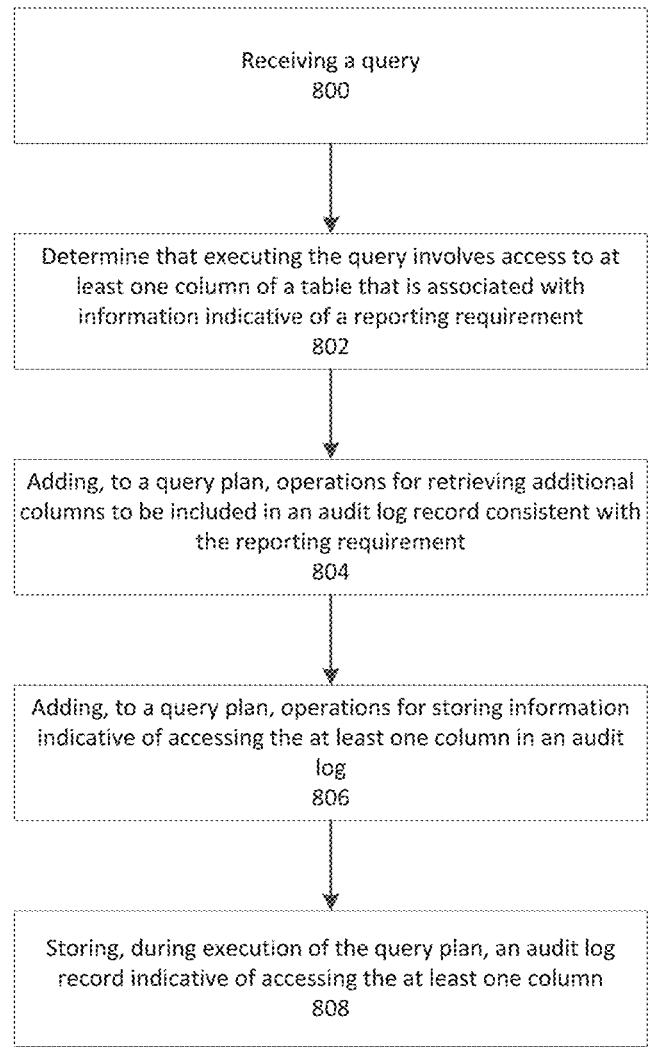
FIG. 8 is a flow diagram depicting auditing access to a table subject to a reporting requirement.

FIG. 8 is a flow diagram depicting auditing access to a table subject to a reporting requirement. Although depicted as a sequence of blocks, those of ordinary skill in the art will appreciate that the depicted order should not be construed as limiting the scope of the present disclosure and that at least some of the operations referred to in the depicted blocks may be altered, omitted, reordered, supplemented with additional operations, or performed in parallel. Embodiments of the depicted process may be implemented using various combinations of computer-executable instructions executed by a computing system, such as the computing systems described herein.

Block 800 depicts receiving a query. The query may be received by a data warehouse component, such as a database management system comprising a query analyzer and a query engine. As depicted by block 802, the database may determine that executing the query will involve accessing at least one column of a table that is subject to a reporting requirement. The column may, for example, be marked as traceable. By the column being so marked, the table is associated with the reporting requirement.

Block 804 depicts the query optimizer adding, to a query plan, operations for retrieving additional columns when those columns are to be included in audit records generated for compliance with the reporting requirement. Block 806 depicts the query optimizer added operations for forming and storing audit logs indicative of access to the columns in the table. The operations may typically store, or cause to be stored, one audit log record for each row of the columns that are accessed. When the query plan is executed, the operations for retrieving data for the auditing, and the operations for storing the audit log records, may be performed. Block 808 depicts this. The query plan may be executed and, during execution, audit log records indicative of accessing the table may be formed and stored. For example, an audit log entry might be generated for each access to a row of a table that is subject to a reporting requirement.

In an embodiment, audit records may be generated for access to selected rows of a table. A column or table subject to a reporting requirement may be associated with a filter that indicates which rows of the table are subject to a reporting requirement. For example, a WHERE clause might identify which rows of a table are subject to a reporting requirement. A query optimizer may incorporate the criteria into its query plan, for example by modifying instructions for retrieving values for a traceable column based on the criteria indicated by the WHERE clause.

Figure 9:
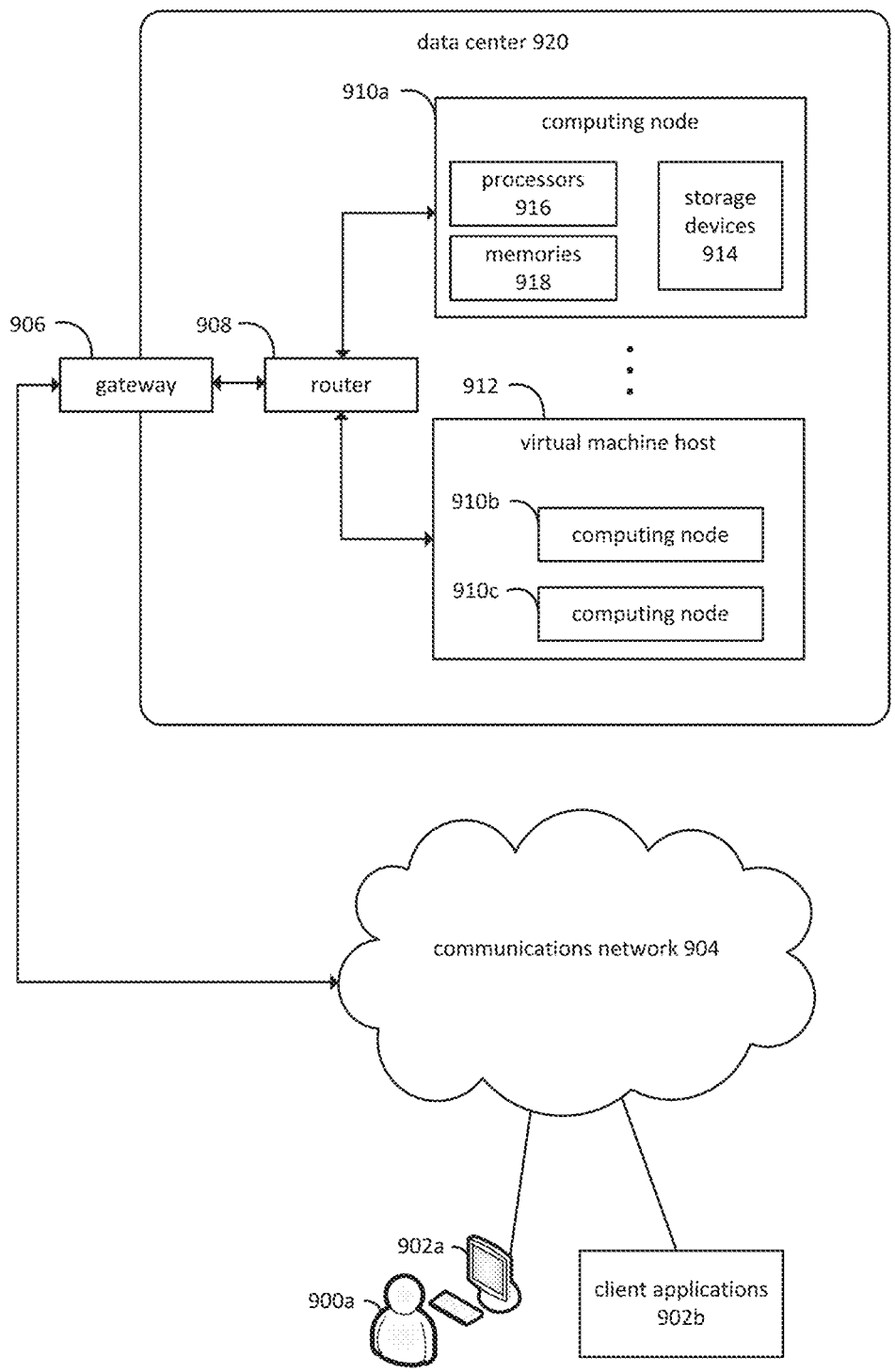
FIG. 9 is a block diagram depicting an embodiment of a computing environment in which aspects of the present disclosure may be practiced.

FIG. 9 is a diagram depicting an example of a distributed computing environment on which aspects of the present invention may be practiced. Various users 900a may interact with various client applications, operating on any type of computing device 902a, to communicate over communications network 904 with processes executing on various computing nodes 910a, 910b, and 910c within a data center 920. Alternatively, client applications 902b may communicate without user intervention. Communications network 904 may comprise any combination of communications technology, including the Internet, wired and wireless local area networks, fiber optic networks, satellite communications, and so forth. Any number of networking protocols may be employed.

Communication with processes executing on the computing nodes 910a, 910b, and 910c, operating within data center 920, may be provided via gateway 906 and router 908. Numerous other network configurations may also be employed. Although not explicitly depicted in FIG. 9, various authentication mechanisms, web service layers, business objects, or other intermediate layers may be provided to mediate communication with the processes executing on computing nodes 910a, 910b, and 910c. Some of these intermediate layers may themselves comprise processes executing on one or more of the computing nodes. Computing nodes 910a, 910b, and 910c, and processes executing thereon, may also communicate with each other via router 908. Alternatively, separate communication paths may be employed. In some embodiments, data center 920 may be configured to communicate with additional data centers, such that the computing nodes and processes executing thereon may communicate with computing nodes and processes operating within other data centers.

Computing node 910a is depicted as residing on physical hardware comprising one or more processors 916, one or more memories 918, and one or more storage devices 914. Processes on computing node 910a may execute in conjunction with an operating system or alternatively may execute as a bare-metal process that directly interacts with physical resources, such as processors 916, memories 918, or storage devices 914.

Computing nodes 910b and 910c are depicted as operating on virtual machine host 912, which may provide shared access to various physical resources, such as physical processors, memory, and storage devices. Any number of virtualization mechanisms might be employed to host the computing nodes.

The various computing nodes depicted in FIG. 9 may be configured to host web services, database management systems, business objects, monitoring and diagnostic facilities, and so forth. A computing node may refer to various types of computing resources, such as personal computers, servers, clustered computing devices, and so forth. A computing node may, for example, refer to various computing devices, such as cell phones, smartphones, tablets, embedded device, and so on. When implemented in hardware form, computing nodes are generally associated with one or more memories configured to store computer-readable instructions and one or more processors configured to read and execute the instructions. A hardware-based computing node may also comprise one or more storage devices, network interfaces, communications buses, user interface devices, and so forth. Computing nodes also encompass virtualized computing resources, such as virtual machines implemented with or without a hypervisor, virtualized bare-metal environments, and so forth. A virtualization-based computing node may have virtualized access to hardware resources as well as non-virtualized access. The computing node may be configured to execute an operating system as well as one or more application programs. In some embodiments, a computing node might also comprise bare-metal application programs.

Figure 10:
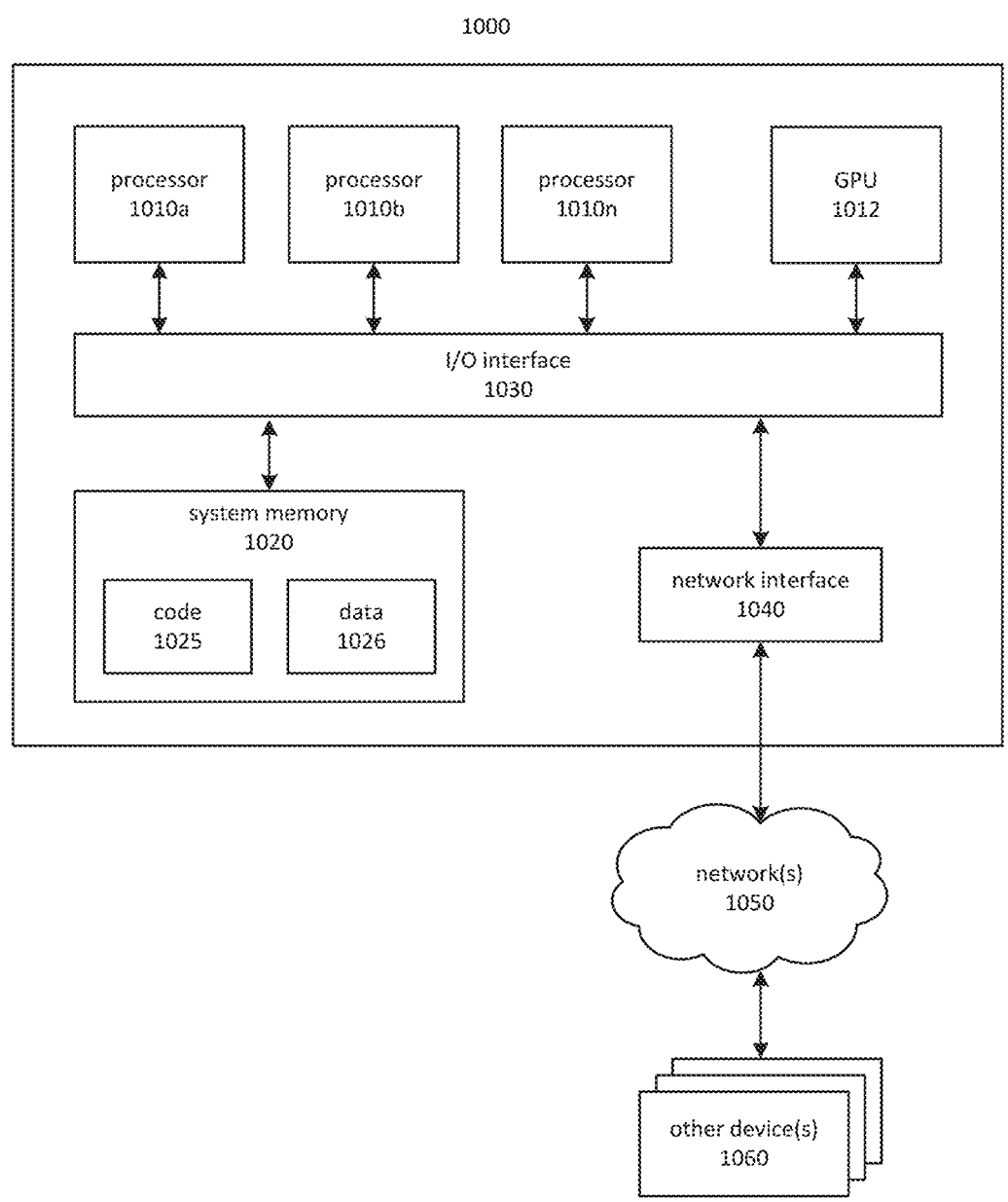
FIG. 10 is a block diagram depicting an embodiment of a computing system on which aspects of the present disclosure may be practiced.

In at least some embodiments, a server that implements a portion or all of one or more of the technologies described herein may include a general-purpose computer system that includes or is configured to access one or more computer-accessible media. FIG. 10 depicts a general-purpose computer system that includes or is configured to access one or more computer-accessible media. In the illustrated embodiment, computing device 1000 includes one or more processors 1010a, 1010b, and/or 1010n (which may be referred herein singularly as a processor 1010 or in the plural as the processors 1010) coupled to a system memory 1020 via an input/output ("I/O") interface 1030. Computing device 1000 further includes a network interface 1040 coupled to I/O interface 1030.

In various embodiments, computing device 1000 may be a uniprocessor system including one processor 1010 or a multiprocessor system including several processors 1010 (e.g., two, four, eight, or another suitable number). Processors 1010 may be any suitable processors capable of executing instructions. For example, in various embodiments, processors 1010 may be general-purpose or embedded processors implementing any of a variety of instruction set architectures ("ISAs"), such as the x86, PowerPC, SPARC or MIPS ISAs, or any other suitable ISA. In multiprocessor systems, each of processors 1010 may commonly, but not necessarily, implement the same ISA.

In some embodiments, a graphics processing unit ("GPU") 1012 may participate in providing graphics rendering and/or physics processing capabilities. A GPU may, for example, comprise a highly parallelized processor architecture specialized for graphical computations. In some embodiments, processors 1010 and GPU 1012 may be implemented as one or more of the same type of device.

System memory 1020 may be configured to store instructions and data accessible by processor(s) 1010. In various embodiments, system memory 1020 may be implemented using any suitable memory technology, such as static random access memory ("SRAM"), synchronous dynamic RAM ("SDRAM"), nonvolatile/Flash®-type memory, or any other type of memory. In the illustrated embodiment, program instructions and data implementing one or more desired functions, such as those methods, techniques, and data described above, are shown stored within system memory 1020 as code 1025 and data 1026.

In one embodiment, I/O interface 1030 may be configured to coordinate I/O traffic between processor 1010, system memory 1020, and any peripherals in the device, including network interface 1040 or other peripheral interfaces. In some embodiments, I/O interface 1030 may perform any necessary protocol, timing or other data transformations to convert data signals from one component (e.g., system memory 1020) into a format suitable for use by another component (e.g., processor 1010). In some embodiments, I/O interface 1030 may include support for devices attached through various types of peripheral buses, such as a variant of the Peripheral Component Interconnect ("PCI") bus standard or the Universal Serial Bus ("USB") standard, for example. In some embodiments, the function of I/O interface 1030 may be split into two or more separate components, such as a north bridge and a south bridge, for example.

Also, in some embodiments some or all of the functionality of I/O interface 1030, such as an interface to system memory 1020, may be incorporated directly into processor 1010.

Network interface 1040 may be configured to allow data to be exchanged between computing device 1000 and other device or devices 1060 attached to a network or networks 1050, such as other computer systems or devices, for example. In various embodiments, network interface 1040 may support communication via any suitable wired or wireless general data networks, such as types of Ethernet networks, for example. Additionally, network interface 1040 may support communication via telecommunications/telephony networks, such as analog voice networks or digital fiber communications networks, via storage area networks, such as Fibre Channel SANs (storage area networks), or via any other suitable type of network and/or protocol.

In some embodiments, system memory 1020 may be one embodiment of a computer-accessible medium configured to store program instructions and data as described above for implementing embodiments of the corresponding methods and apparatus. However, in other embodiments, program instructions and/or data may be received, sent, or stored upon different types of computer-accessible media. Generally speaking, a computer-accessible medium may include non-transitory storage media or memory media, such as magnetic or optical media, e.g., disk or DVD/CD coupled to computing device 1000 via I/O interface 1030. A non-transitory computer-accessible storage medium may also include any volatile or non-volatile media, such as RAM (e.g., SDRAM, DDR SDRAM, RDRAM, SRAM, etc.), ROM, etc., that may be included in some embodiments of computing device 1000 as system memory 1020 or another type of memory. Further, a computer-accessible medium may include transmission media or signals, such as electrical, electromagnetic or digital signals, conveyed via a communication medium, such as a network and/or a wireless link, such as those that may be implemented via network interface 1040. Portions or all of multiple computing devices, such as those illustrated in FIG. 10, may be used to implement the described functionality in various embodiments; for example, software components running on a variety of different devices and servers may collaborate to provide the functionality. In some embodiments, portions of the described functionality may be implemented using storage devices, network devices or special-purpose computer systems, in addition to or instead of being implemented using general-purpose computer systems. The term "computing device," as used herein, refers to at least all these types of devices and is not limited to these types of devices.

A compute node, which may be referred to also as a computing node, may be implemented on a wide variety of computing environments, such as tablet computers, personal computers, smartphones, game consoles, commodity-hardware computers, virtual machines, web services, computing clusters, and computing appliances. Any of these computing devices or environments may, for convenience, be described as compute nodes or as computing nodes.

A network set up by an entity, such as a company or a public sector organization, to provide one or more web services (such as various types of cloud-based computing or storage) accessible via the Internet and/or other networks to a distributed set of clients may be termed a provider network. Such a provider network may include numerous data centers hosting various resource pools, such as collections of physical and/or virtualized computer servers, storage devices, networking equipment, and the like, needed to implement and distribute the infrastructure and web services offered by the provider network. The resources may in some embodiments be offered to clients in various units related to the web service, such as an amount of storage capacity for storage, processing capability for processing, as instances, as sets of related services, and the like. A virtual computing instance may, for example, comprise one or more servers with a specified computational capacity (which may be specified by indicating the type and number of CPUs, the main memory size, and so on) and a specified software stack (e.g., a particular version of an operating system, which may in turn run on top of a hypervisor).

A number of different types of computing devices may be used singly or in combination to implement the resources of the provider network in different embodiments, including general-purpose or special-purpose computer servers, storage devices, network devices, and the like. In some embodiments a client or user may be provided direct access to a resource instance, e.g., by giving a user an administrator login and password. In other embodiments the provider network operator may allow clients to specify execution requirements for specified client applications and schedule execution of the applications on behalf of the client on execution platforms (such as application server instances, Java™ virtual machines ("JVMs"), general-purpose or special-purpose operating systems, platforms that support various interpreted or compiled programming languages, such as Ruby, Perl, Python, C, C++, and the like, or high-performance computing platforms) suitable for the applications, without, for example, requiring the client to access an instance or an execution platform directly. A given execution platform may utilize one or more resource instances in some implementations; in other implementations multiple execution platforms may be mapped to a single resource instance.

In many environments, operators of provider networks that implement different types of virtualized computing, storage and/or other network-accessible functionality may allow customers to reserve or purchase access to resources in various resource acquisition modes. The computing resource provider may provide facilities for customers to select and launch the desired computing resources, deploy application components to the computing resources, and maintain an application executing in the environment. In addition, the computing resource provider may provide further facilities for the customer to quickly and easily scale up or scale down the numbers and types of resources allocated to the application, either manually or through automatic scaling, as demand for or capacity requirements of the application change. The computing resources provided by the computing resource provider may be made available in discrete units, which may be referred to as instances. An instance may represent a physical server hardware platform, a virtual machine instance executing on a server, or some combination of the two. Various types and configurations of instances may be made available, including different sizes of resources executing different operating systems ("OS") and/or hypervisors, and with various installed software applications, runtimes, and the like. Instances may further be available in specific availability zones, representing a logical region, a fault tolerant region, a data center, or other geographic location of the underlying computing hardware, for example. Instances may be copied within an availability zone or across availability zones to improve the redundancy of the instance, and instances may be migrated within a particular availability zone or across availability zones. As one example, the latency for client communications with a particular server in an availability zone may be less than the latency for client communications with a different server. As such, an instance may be migrated from the higher latency server to the lower latency server to improve the overall client experience.

In some embodiments the provider network may be organized into a plurality of geographical regions, and each region may include one or more availability zones. An availability zone (which may also be referred to as an availability container) in turn may comprise one or more distinct locations or data centers, configured in such a way that the resources in a given availability zone may be isolated or insulated from failures in other availability zones. That is, a failure in one availability zone may not be expected to result in a failure in any other availability zone. Thus, the availability profile of a resource instance is intended to be independent of the availability profile of a resource instance in a different availability zone. Clients may be able to protect their applications from failures at a single location by launching multiple application instances in respective availability zones. At the same time, in some implementations inexpensive and low latency network connectivity may be provided between resource instances that reside within the same geographical region (and network transmissions between resources of the same availability zone may be even faster).

Each of the processes, methods, and algorithms described in the preceding sections may be embodied in, and fully or partially automated by, code modules executed by one or more computers or computer processors. The code modules may be stored on any type of non-transitory computer-readable medium or computer storage device, such as hard drives, solid state memory, optical disc, and/or the like. The processes and algorithms may be implemented partially or wholly in application-specific circuitry. The results of the disclosed processes and process steps may be stored, persistently or otherwise, in any type of non-transitory computer storage, such as, e.g., volatile or non-volatile storage.

The various features and processes described above may be used independently of one another, or may be combined in various ways. All possible combinations and sub-combinations are intended to fall within the scope of this disclosure. In addition, certain methods or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

It will also be appreciated that various items are illustrated as being stored in memory or on storage while being used, and that these items or portions thereof may be transferred between memory and other storage devices for purposes of memory management and data integrity. Alternatively, in other embodiments some or all of the software modules and/or systems may execute in memory on another device and communicate with the illustrated computing systems via inter-computer communication. Furthermore, in some embodiments, some or all of the systems and/or modules may be implemented or provided in other ways, such as at least partially in firmware and/or hardware, including, but not limited to, one or more application-specific integrated circuits ("ASICs"), standard integrated circuits, controllers (e.g., by executing appropriate instructions, and including microcontrollers and/or embedded controllers), field-programmable gate arrays ("FPGAs"), complex programmable logic devices ("CPLDs"), etc. Some or all of the modules, systems, and data structures may also be stored (e.g., as software instructions or structured data) on a computer-readable medium, such as a hard disk, a memory, a network, or a portable media article to be read by an appropriate device or via an appropriate connection. The systems, modules, and data structures may also be transmitted as generated data signals (e.g., as part of a carrier wave or other analog or digital propagated signal) on a variety of computer-readable transmission media, including wireless-based and wired/cable-based media, and may take a variety of forms (e.g., as part of a single or multiplexed analog signal, or as multiple discrete digital packets or frames). Such computer program products may also take other forms in other embodiments. Accordingly, the present invention may be practiced with other computer system configurations.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

What is claimed is:

1. A data warehouse system comprising a computing node, wherein the computing node at least:
 receives a query of a database comprising a plurality of tables;
 determines that processing the query involves accessing a second column of a row of a table of the plurality of tables, and that a first column of the row indicates that data in the table is subject to auditing, wherein retrieval of the first column is not indicated by the received query, wherein auditing includes writing, to a log, information identifying the table that was accessed;

forms, in response to the determination and based at least in part on the first column indicating that data in the table is subject to auditing, a query plan comprising instructions to retrieve one or more values of the second column based on the query and instructions to retrieve one or more values of the first column;

executes the query plan; and writes, to the log and based at least in part on determining that processing the query involves accessing the second column and that the first column indicates data in the table is subject to auditing, information indicative of the accessing the second column, the information comprising a value for the first column of the row, the value obtained by executing the query plan.

2. The system of claim 1, wherein the computing node at least:

forms the query plan to comprise instructions for retrieving the value of the first column of the row; and forms the query plan to comprise instructions for writing, to the log, the information indicative of the access to the second column.

3. The system of claim 1, wherein the computing node at least:

receives a data definition language statement comprising a definition of the first column, the definition comprising the information indicative of auditing access to the table; and stores the information indicative of auditing access to the table in response to receiving the data definition language statement.

4. The system of claim 1, wherein the log comprises a file comprising values for the first column of the table.

5. The system of claim 1, wherein the computing node at least:

writes the information indicative of accessing the second column when the first column and the second column are not included in projections defined by the query.

6. A method, comprising:

receiving a query of a database comprising a plurality of tables;

determining that executing the query involves accessing a second column of a row of a table of the plurality of tables, and that the table comprises a first column indicating that data in the table is subject to auditing, wherein the query does not comprise a projection that includes the first column;

adding instructions for retrieving values of the first column to a query plan based at least in part on determining that the query involves accessing the second column and based on determining that the table is subject to auditing; and storing information indicative of accessing the second column of the row while executing the query plan, the information comprising a value for the first column of the row, the value obtained by the executing of the query plan.

7. The method of claim 6, wherein the query plan comprises instructions for retrieving values of the first column for all rows of the table accessed when the query plan is executed.

8. The method of claim 6, further comprising:

receiving a data definition language statement comprising a definition of the first column, the definition comprising the information indicative of auditing access to the table; and storing the information indicative of auditing access to the table in response to receiving the data definition language statement.

9. The method of claim 6, further comprising:

storing the information indicative of accessing the second column of the row, the information indicative stored in a second table comprising the first column.

10. The method of claim 6, further comprising:

writing the information indicative of accessing the second column of the row when the first column is absent from projections defined by the query.

11. The method of claim 6, further comprising:

determining that executing the query involves accessing the second column of a second row of the table; and determining, based on a filter criteria, to not store information indicative of access to the second column of the second row.

12. The method of claim 6, wherein the information indicative of accessing the second column of the row comprises a time and date of the access.

13. The method of claim 6, further comprising:

forming the table from a first source table and a second source table, wherein the first source table comprises the second column and access to the first source table is audited; and storing the information indicative of auditing access to the table in response to determining that the first source table is audited.

14. A non-transitory computer-readable storage medium comprising instructions that, upon execution by one or more computing devices, cause the one or more computing devices at least to:

receive a query of a database comprising a table;

determine that execution of the query involves access to a second column of a row of the table, and that the table comprises a first column indicating that data in the table is subject to auditing;

add, as a result of determining that the query involves accessing the second column, instructions for retrieving values of the first column to a query plan comprising instructions for processing the query; and store information indicative of an access to the second column of the row, the information comprising a value of the first column of the row obtained by executing the query plan.

15. The non-transitory computer-readable storage medium of claim 14, wherein the query plan comprises instructions for retrieving values of the first column for all rows of the table accessed when the query plan is executed.

16. The non-transitory computer-readable storage medium of claim 14, wherein the information indicative of the access to the second column is stored in a file comprising values for the first column of the table.

17. The non-transitory computer-readable storage medium of claim 14, comprising further instructions that, upon execution by the one or more computing devices, cause the one or more computing devices to at least:

write the information indicative of the access to the second column of the row when the first column is absent from results of executing the query.

18. The non-transitory computer-readable storage medium of claim 14, comprising further instructions that, upon execution by the one or more computing devices, cause the one or more computing devices to at least:

determine that executing the query involves accessing the second column of a second row of the table; and determine, based on a criteria, to not store a record of accessing the second column of the second row.

19. The non-transitory computer-readable storage medium of claim 14, wherein the information indicative of the access to the second column comprises at least one of a time and date of the access, a user associated with the access, or a reason for the access.

20. The non-transitory computer-readable storage medium of claim 14, comprising further instructions that, upon execution by the one or more computing devices, cause the one or more computing devices to at least:
   form the table from a first source table and a second source table, wherein the first source table comprises the second column and the first source table is audited; and
   store the information indicative of auditing access to the table in response to determining that the first source table is audited.

* * * * *